(12) United States Patent
Nilsen et al.

(10) Patent No.: US 8,232,049 B2
(45) Date of Patent: Jul. 31, 2012

(54) METHOD FOR DETECTING SMALL OLIGONUCLEOTIDES

(75) Inventors: Timothy W. Nilsen, Chagrin Falls, OH (US); Patricia A. Maroney, Chagrin Falls, OH (US); Sangpen Chamnongpol, Streetsboro, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 11/862,272

(22) Filed: Sep. 27, 2007

(65) Prior Publication Data

US 2008/0176233 A1    Jul. 24, 2008

Related U.S. Application Data

(60) Provisional application No. 60/848,236, filed on Sep. 29, 2006.

(51) Int. Cl.
  *C12Q 1/68*  (2006.01)
  *C07H 21/04* (2006.01)
  *C07H 21/02* (2006.01)

(52) U.S. Cl. ..... 435/6; 536/23.1; 536/24.31; 536/24.33; 536/24.5

(58) Field of Classification Search ............ None
See application file for complete search history.

(56) References Cited

U.S. PATENT DOCUMENTS

| | | | | |
|---|---|---|---|---|
| 4,683,194 | A * | 7/1987 | Saiki et al. | 435/6 |
| 2005/0048498 | A1 * | 3/2005 | Woudenberg et al. | 435/6 |
| 2005/0064459 | A1 * | 3/2005 | Lao | 435/6 |
| 2006/0019258 | A1 * | 1/2006 | Yeakley | 435/6 |
| 2006/0094025 | A1 * | 5/2006 | Getts et al. | 435/6 |
| 2007/0003940 | A1 * | 1/2007 | Wang | 435/6 |

FOREIGN PATENT DOCUMENTS

| | | |
|---|---|---|
| WO | WO 97/25444 | 7/1997 |
| WO | WO 01/34845 A1 | 5/2001 |
| WO | WO 2006/050433 A3 | 5/2006 |
| WO | WO 2007/024653 A2 | 3/2007 |

OTHER PUBLICATIONS

Kurschat, Wolfram C., et al., "Optimizing splinted ligation of highly structured small RNAs", RNA (2005), 11:1909-1914. Published by Cold Spring Harbor Laboratory Press.

Moore, Melissa J., "Joining of RNAs by Splinted Ligation", Methods in Enzymology, vol. 317.

* cited by examiner

*Primary Examiner* — Amy Bowman
(74) *Attorney, Agent, or Firm* — Tarolli, Sundheim, Covell & Tummino LLP

(57) ABSTRACT

A method for detecting small oligonucleotides includes providing a biological isolate containing at least one small oligonucleotide. The biological isolate may be contacted with at least one detection oligonucleotide having a label moiety and at least one bridge oligonucleotide under conditions such that the at least one small oligonucleotide and the at least one detection oligonucleotide are preferentially added to the bridge oligonucleotide to produce at least one labeled small oligonucleotide. At least one ligating reagent may be added to preferentially join the at least one small oligonucleotide and the at least one detection oligonucleotide. The at least one labeled small oligonucleotide may then be detected.

18 Claims, 5 Drawing Sheets

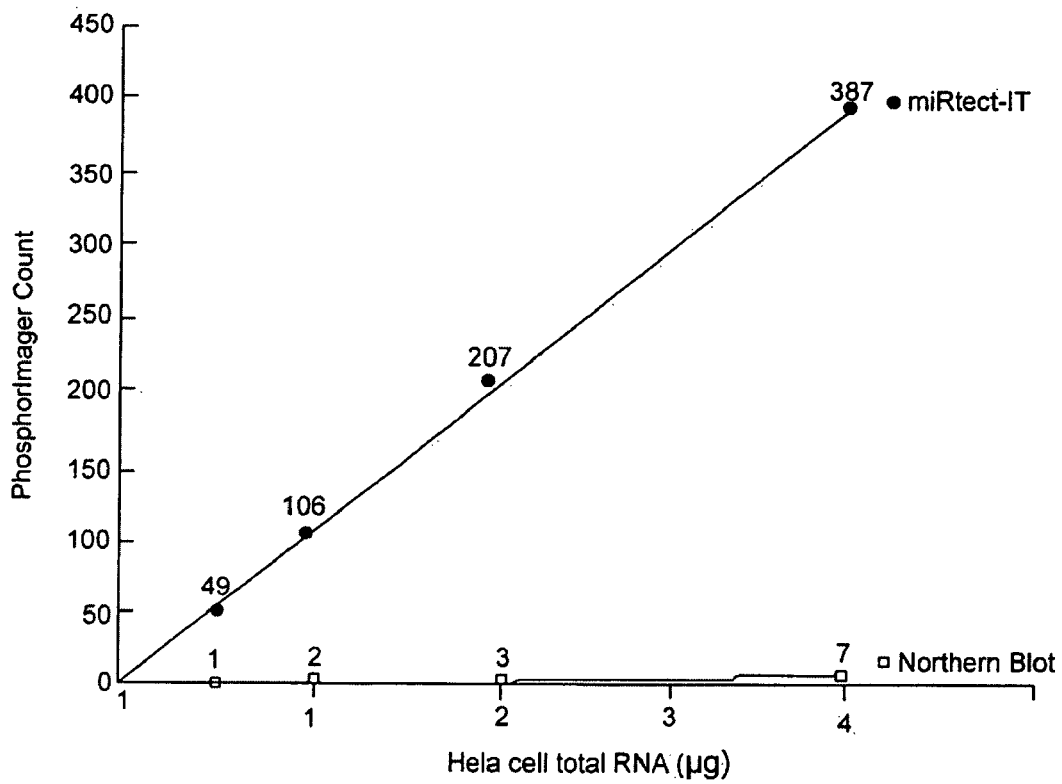
Fig. 2B-C

US 8,232,049 B2

METHOD FOR DETECTING SMALL OLIGONUCLEOTIDES

RELATED APPLICATIONS

The present application claim priority from U.S. Provisional Patent Application Ser. No. 60/848,236 filed Sep. 29, 2006, which is herein incorporated by reference in its entirety.

GOVERNMENT INTEREST

This invention was made with government support under NIH Grant Nos. GM31528 and AI28799 awarded by the National Institute of Health (NIH). The United States government may have certain rights in the invention.

TECHNICAL FIELD

The present invention generally relates to methods for detecting nucleic acids, and more particularly to methods for detecting small oligonucleotides, such as small regulatory RNAs, microRNA, and small interfering RNA.

BACKGROUND OF THE INVENTION

Small regulatory RNAs, such as microRNAs (miRNAs), are a family of 21-25 nucleotide non-coding RNAs that regulate gene expression at the post-transcriptional level. Interaction between the miRNA and its mRNA target often results in inhibition of protein synthesis. To date, more than 1,000 miRNAs have been identified in animals and plants according to the miRNA registry. Growing evidence suggests that miRNAs are important regulators of cell division and differentiation as well as human cancer genes. Recently, the discovery of regulatory effects on gene expression has led to numerous studies on the characterization of miRNA function in molecular processes and as possible tools in drug discovery.

Interest in small regulatory RNAs, such as miRNAs, has created demand for novel tools to study expression. Presently, Northern blot is the standard technique for small RNA expression analysis. The main advantage of Northern blotting is that it does not require an amplification step that may artificially generate false positives. However, a major drawback of Northern blots is poor sensitivity, especially when monitoring expression of short nucleotide sequences such as miRNAs. In addition, a large amount of total RNA is often required for Northern blots. Despite improvements in detection such as using locked nucleic acid probes, the procedures for Northern blot assay remain labor intensive and time-consuming.

SUMMARY OF THE INVENTION

The present invention relates to a method for detecting a plurality of different small oligonucleotides. The method includes providing a biological isolate comprising at least one small oligonucleotide. The biological isolate may be contacted with at least one detection oligonucleotide having a label moiety and at least one bridge oligonucleotide under conditions such that the at least one small oligonucleotide and the at least one detection oligonucleotide are preferentially added to the bridge oligonucleotide to produce at least one labeled small oligonucleotide. At least one ligating reagent may be added to preferentially join the at least one small oligonucleotide and the at least one detection oligonucleotide. The at least one labeled small oligonucleotide may then be detected.

In another aspect of the present invention, a kit is provided for detecting a plurality of small oligonucleotides in a biological isolate. The kit includes a detection oligonucleotide comprising about 5 to about 500 oligonucleotides (e.g. about 5 to about 50 nucleotides) and having a 5' end and a 3' end. The detection oligonucleotide preferentially ligates to the small oligonucleotide. The kit may also include a label moiety for preferentially labeling the detection oligonucleotide. The label moiety may be linked to the detection oligonucleotide. Further, the kit may include reagents for ligating the small oligonucleotide to the detection oligonucleotide.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2A-C show the quantitative expression of miR-21 using the present invention (FIG. 2A, upper) and Northern blot (FIG. 2A, lower). The assays represented in FIG. 2A were performed in parallel using HeLa cell total RNA with the indicated amounts. Images were quantified using phosphorimager analysis (FIG. 2B). FIG. 2C is a table showing the experimental parameters and the resultant sensitivities of each assay;

FIG. 3B is a table comparing experimental parameters between the present invention and Northern blot assay; FIGS. 4A-B show detection of miR-124a and miR-133a-1 by the present invention (FIG. 4A) and solution hybridization/ribonuclease protection assay (FIG. 4B). Both assays were performed in parallel using total RNA with the indicated amounts. The image was developed after 2 hr X-ray film exposure at −80° C. FIG. 4C is a table comparing the experimental parameters and resultant sensitivities of the present invention and the solution hybridization/ribonuclease protection assay.

DETAILED DESCRIPTION

Figure 1:
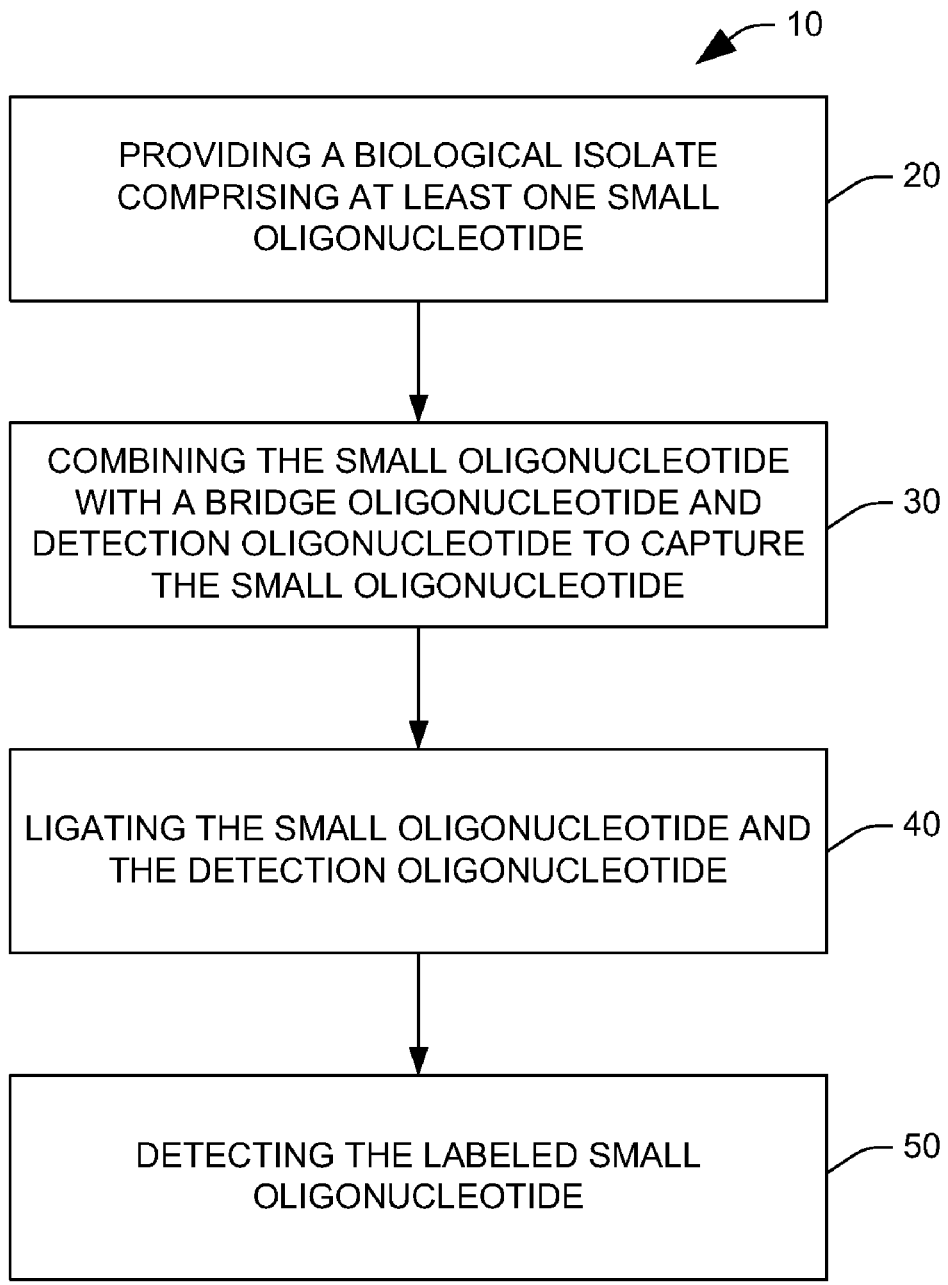
FIG. 1 is a flowchart showing a process for detecting a plurality of small oligonucleotides according to one aspect of the present invention.

The present invention relates generally to methods for detecting nucleic acids, and more particularly to methods for detecting small oligonucleotides, such as small regulatory RNAs (e.g., microRNA (miRNA) and small interfering RNA (siRNA)). It was discovered that a labeled detection oligonucleotide in combination with a bridge oligonucleotide can be used to detect small oligonucleotides, such as small regulatory RNAs (e.g., miRNAs and siRNAs). Based on this discovery, the present invention provides a method for detecting multiple small oligonucleotides in, for example, about 50 ng or less of total RNA without the need for an amplification step. Advantageously, the method of the present invention is fast (e.g., capturing and labeling small oligonucleotides in just over 2 hours) and has a linear detection range of about 0.1 to about 10 femtomoles.

The present invention also allow for the simultaneous detection of several small oligonucleotides. Because several small oligonucleotides can be simultaneously detected, the diversity of small oligonucleotides present in a cell or organism can be readily evaluated in a research or clinical setting using the present invention.

As used herein, the term "small oligonucleotide" is intended to mean a nucleic acid having a length of about 5 to about 500 nucleotides, (e.g., about 5 about to about 50 nucleotides, about 5 to about 30 nucleotides, or about 10 to about 30 nucleotides), and terminating in a 5' phosphate and/or a 3' hydroxyl. A 5' phosphate is understood to be a $(PO_4)^{2-}$ $(PO_4H)^-$ or $(PO_4H_2)$ moiety covalently attached to the 5' carbon of ribose via one of the oxygens. A 3' hydroxyl is understood to be an OH or O— moiety covalently attached to the 3' carbon of ribose via the oxygen. Those skilled in the art will recognize that the presence or absence of hydrogen in the phosphate and hydroxyl moieties as listed above is a function of their pKa values and the pH of their environment.

Small oligonucleotides can be identified according to their function in a cell including, for example, having a non-coding sequence (i.e., not being translated into protein) (e.g., non-coding RNA) and being capable of regulating expression of at least one gene (e.g., small regulatory RNA). Small oligonucleotides can also be identified according to their biosynthesis. For example, one type of small oligonucleotide, siRNA, is typically synthesized from endogenous or exogenous double-stranded RNA (dsRNA) molecules having hairpin structures and processed such that numerous siRNA molecules are produced from both strands of the hairpin. In contrast, miRNA molecules are typically produced from endogenous dsRNA molecules having one or more hairpin structure such that a single miRNA molecule is produced from each hairpin structure. The terms "siRNA" and "miRNA" are intended to be consistent with their use in the art as described, for example, in Ambros et al., RNA 9:277-279 (2003).

Where a small oligonucleotide comprises small regulatory RNA, such as siRNA or miRNA, the small oligonucleotide can be distinguished from mRNA based on the presence of a 5' cap structure in mRNA and absence of the cap structure in the small oligonucleotide. The 5' cap structure typically found in eukaryotic mRNA is a 7-methylguanylate having a 5' to 5' triphosphate linkage to the terminal nucleotide. Small interfering RNA molecules or miRNAs can also be distinguished from mRNA based on the presence of a terminal polyadenylate sequence at the 3' end of mRNA which is absent in siRNAs and miRNAs.

As used herein, the term "biological isolate" is intended to mean one or more substances removed from at least one co-occurring molecule of an organism. An isolated nucleic acid can be, for example, essentially free of other nucleic acids such that it is increased to a significantly higher fraction of the total nucleic acid present in the biological isolate than in the cells from which it was taken. For example, an isolated nucleic acid can be enriched at least 2, 5, 10, 50, 100, 1000 fold or higher in the biological isolate compared to in the cell from which it was taken. A biological isolate can be obtained from an intact organism, tissue or cell. Examples of eukaryotes from which biological isolates can be derived in a method of the invention include, without limitation, a mammal, such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*Oryza sativa*), wheat, rice, canola, or soybean; an algae, such as *Chlamydomonas reinhardtii*; a nematode such as *Caenorhabditis elegans*; an insect, such as *Drosophila melanogaster*, mosquito, fruit fly, honey bee or spider; a fish such as zebrafish (*Danio rerio*); a reptile; an amphibian such as a frog or *Xenopus laevis*; a dictyostelium discoideum; a fungi, such as *Pneumocystis carinii, Takifugu rubripes*, yeast, *Saccharamoyces cerevisiae* or *Schizosaccharomyces pombe*; or *Plasmodium falciparum*. In addition to animal and plant systems, the present invention can be used with a prokaryote system including, for example, a bacterium such as *Escherichia coli*, Staphylococci or *Mycoplasma pneumoniae*; an archae; a virus such as Hepatitis C virus or human immunodeficiency virus; or a viroid. Endogenous small oligonucleotides can be isolated from a biological system from which they were synthesized. Exogenous small oligonucleotides can be isolated from a biological system from which they were transmitted, for example, by viral infection or treatment with a small oligonucleotide precursor. Exemplary small oligonucleotide precursors include dsRNAs, such as those described in further detail below.

As used herein, the term "detection oligonucleotide" is intended to mean a nucleotide sequence comprising about 5 to about 500 nucleotides (e.g., about 5 to about 200 nucleotides, about 5 to about 100 nucleotides, or about 5 to about 50 nucleotides), and terminating in a 5' end and a 3' end. In one aspect of the present invention, the detection oligonucleotide may include a 5' phosphate and a modified 3' end. A 5' phosphate is understood to be a $(PO_4)^{2-}$ $(PO_4H)^-$ or $(PO_4H_2)$ moiety covalently attached to the 5' carbon of ribose via one of the oxygens. In another aspect of the present invention, the detection oligonucleotide may include a 3' hydroxyl and a modified 5' end. A 3' hydroxyl is understood to be an OH or O— moiety covalently attached to the 3' carbon of ribose via the oxygen. Those skilled in the art will recognize that the presence or absence of hydrogen in the phosphate and hydroxyl moieties as listed above is a function of their pKa values and the pH of their environment.

A modified 5' or 3' end may include any chemical or structural modification of at least one nucleotide that may prevent, inhibit and/or reduce phosphodiester bond formation between two nucleotides. Examples of such modifications include, without limitation, C-3 spacers, amino modifiers, inverted dTs, and dideoxy-Cs. By including a modified 5' or 3' end, formation of unwanted side ligation products may be reduced or prevented.

The detection oligonucleotide may be comprised of naturally occurring or synthetic RNA, DNA, or other oligonucleotides such as an analog of a naturally occurring nucleic acid. At least one locked nucleic acid (LNA) molecule may also be included in the detection oligonucleotide. A LNA can include a modified RNA nucleotide, for example, in which the ribose moiety of the LNA is modified with an extra bridge connecting the 2' and 4' carbons. The bridge may lock the ribose in a 3'-endo structural conformation, thereby enhancing base stability and backbone pre-organization.

A nucleic acid analog can have an alternate backbone including, without limitation, phosphoramide (see, for example, Beaucage et al., Tetrahedron 49:1925 (1993); Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 (1986)), phosphorothioate (see, for example, Mag et al., Nucleic Acids Res. 19:1437 (1991); and U.S. Pat. No. 5,644,048), phosphorodithioate (see, for example, Briu et al., J. Am. Chem. Soc. 111:2321 (1989)), O-methylphosphoroamidite linkages (see, for example, Eckstein, Oligonucleotides and Analogues: A Practical Approach, Oxford University Press), and peptide nucleic acid backbones and linkages (see, for example, Egholm, J. Am. Chem. Soc. 114:1895 (1992); Meier et al., Chem. Int. Ed. Engl. 31:1008 (1992); Nielsen, Nature, 365:

566 (1993); Carlsson et al., Nature 380:207 (1996)). Other analog structures include those with positive backbones (see, for example, Dempcy et al., Proc. Natl. Acad. Sci. USA 92:6097 (1995); non-ionic backbones (see, for example, U.S. Pat. Nos. 5,386,023; 5,637,684; 5,602,240; 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996) and non-ribose backbones, including, for example, those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Analog structures containing one or more carbocyclic sugars are also useful in the methods and are described, for example, in Jenkins et al., Chem. Soc. Rev. (1995) pp 169-176. Several other analog structures that are useful in the invention are described in Rawls, C & E News Jun. 2, 1997 page 35. Similar analogs can be used in a probe or other nucleic acid of the invention.

A nucleic acid or nucleic acid analog used in the present invention can include native or non-native bases or both. Native deoxyribonucleic acid bases include adenine, thymine, cytosine or guanine and native ribonucleic acid bases include uracil, adenine, cytosine or guanine. Exemplary non-native bases that can be used in the invention include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like.

As used herein, the term "bridge oligonucleotide" is intended to mean a nucleotide sequence comprising about 10 to 100 nucleotides or longer, and terminating in a 5' end and a 3' end. The bridge oligonucleotide can include naturally occurring or synthetic RNA, DNA, or other oligonucleotide, such as an analog of a naturally occurring nucleic acid (described in detail above). Both the 5' and 3' ends of the bridge oligonucleotide may include a modification, such a C-3 spacer, inverted dT, amino modifier, dideoxy-C, or another agent to reduce or prevent the formation of unwanted side ligation products. Alternatively, the 5' and 3' ends may respectively include a 5' phosphate and a 3' hydroxyl; however, such end groups are not preferred as there may be a greater chance of generating side ligation products. The bridge oligonucleotide can be complementary to both the detection oligonucleotide and a small oligonucleotide at the 5' and 3' ends, respectively. Alternatively, the bridge oligonucleotide can be complementary to both the detection oligonucleotide and a small oligonucleotide at the 3' and 5' ends, respectively. Further, a portion of the bridge oligonucleotide between the 5' and 3' ends may be complementary to the small oligonucleotide, while the 5' and 3' ends may be complementary to a plurality of detection oligonucleotides.

As used herein, the term "label moiety" is intended to mean one or more atom(s) that can be specifically detected to identify a substance, such as a nucleic acid, to which the one or more atom(s) is/are attached. A label moiety can be a primary label that is directly detectable or secondary label that can be indirectly detected, for example, via interaction with a primary label. Exemplary primary labels include, without limitation, an isotopic label, such as a naturally non-abundant heavy isotope or radioactive isotope examples of which include $^{14}C$, $^{123}I$, $^{124}I$, $^{125}I$, $^{131}I$, $^{32}P$, $^{33}P$, $^{35}S$ or $^{3}H$; optically detectable moieties, such as a chromophore, luminophore, fluorophore, quantum dot or nanoparticle light scattering label; electromagnetic spin label; calorimetric agent; magnetic substance; electron-rich material, such as a metal; electrochemiluminescent label, such as $Ru(bpy)_3^{2+}$; moiety that can be detected based on a nuclear magnetic, paramagnetic, electrical, charge to mass, or thermal characteristic; or light scattering or plasmon resonant materials such as gold or silver particles. Fluorophores that can be used in the invention include, for example, fluorescent lanthanide complexes, including those of Europium and Terbium, fluorescein, fluorescein isothiocyanate, dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, CASCADE BLUE, Texas Red, alexa dyes, dansyl chloride, phycoerythin, green fluorescent protein and its wavelength shifted variants, bodipy, and others known in the art, such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

Examples of secondary labels are binding moieties, such as a receptor, ligand or other member of a pair of molecules having binding specificity for each other. Exemplary binding moieties having specificity for each other include, without limitation, streptavidin/biotin, avidin/biotin or an antigen/antibody complex such as rabbit IgG and anti-rabbit IgG. Specific affinity between two binding partners is understood to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-4}$, $10^{-5}$, $10^{-6}$, $10^{-7}$, $10^{-8}$, $10^{-9}$, $10^{-10}$, $10^{-11}$, or $10^{-12}$ $M^{-1}$. Secondary labels also include enzymes that produce a detectable product such as horseradish peroxidase, alkaline phosphatase, β-galactosidase, or acetylcholinesterase.

As used herein, the term "ligand" is intended to mean a molecule that is capable of selectively binding to another molecule.

FIG. 1 is a flow diagram illustrating a method 10 for detecting small oligonucleotides in accordance with an aspect of the invention. In the method 10, at 20, a biological isolate comprising at least one small oligonucleotide is provided. The biological isolate can be from any of a variety of organisms including, without limitation, those set forth above. In many cases, biological isolates can be available from commercial sources or from banks and depositories administered by public or private institutions such as the American Type Culture Collection (ATCC). For many applications, it is desirable that isolation protocols used by commercial sources are not biased against retention of small oligonucleotides of interest for a particular application of the present invention. A biological isolate can be from one or more cells, bodily fluids or tissues. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues, such as buccal swab, mouthwash, surgical removal, biopsy aspiration or the like. A biological isolate can also be obtained from one or more cell or tissue in primary culture, in a propagated cell line, a fixed archival sample, forensic sample or archeological sample.

Exemplary cell types from which a nucleic acid-containing isolate can be obtained in the method 10 of the present invention can include, without limitation, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which an isolate is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cell (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally, any type of stem cell can be used including, without limitation, an embryonic stem cell, adult stem cell, or pluripotent stem cell.

A cell from which a biological isolate is obtained for use in the present invention can be a normal cell or a cell displaying one or more symptom of a particular disease or condition. Thus, a biological isolate used in a method of the present invention can be obtained from a cancer cell, neoplastic cell, necrotic cell or cell experiencing a disease or condition set forth below. Those skilled in the art will know or be able to readily determine methods for isolating samples from a cell, fluid or tissue using methods known in the art such as those described in Sambrook et al., Molecular Cloning: A Laboratory Manual, 3rd edition, Cold Spring Harbor Laboratory, New York (2001) or in Ausubel et al., Current Protocols in Molecular Biology, John Wiley and Sons, Baltimore, Md. (1998).

Another aspect of the present invention can further include steps of isolating a particular type of cell or tissue. Exemplary methods that can be used to isolate a particular cell from other cells in a population include, but are not limited to, Fluorescent Activated Cell Sorting (FACS) as described, for example, in Shapiro, Practical Flow Cytometry, 3rd edition Wiley-Liss; (1995), density gradient centrifugation, or manual separation using micromanipulation methods with microscope assistance. Exemplary cell separation devices that are useful in the invention include, without limitation, a Beckman JE-6 centrifugal elutriation system, Beckman Coulter EPICS ALTRA computer-controlled Flow Cytometer-cell sorter, Modular Flow Cytometer from Cytomation, Inc., Coulter counter and channelyzer system, density gradient apparatus, cytocentrifuge, Beckman J-6 centrifuge, EPICS V dual laser cell sorter, or EPICS PROFILE flow cytometer. A tissue or population of cells can also be removed by surgical techniques. For example, a tumor or cells from a tumor can be removed from a tissue by surgical methods, or conversely non-cancerous cells can be removed from the vicinity of a tumor.

A biological isolate can be prepared for use in the method 10 of the present invention by lysing a cell that contains one or more desired nucleic acids. Typically, a cell is lysed under conditions that substantially preserve the integrity of the desired nucleic acid. For example, cells can be lysed or subfractions obtained under conditions that stabilize RNA integrity. Such conditions include, for example, cell lysis in strong denaturants, including chaotropic salts such as guanidine thiocyanate, ionic detergents such as sodium dodecyl sulfate, organic solvents such as phenol, high lithium chloride concentrations or other conditions known in the art to be effective in limiting the activity of endogenous RNases during RNA purification as described, for example, in Sambrook et al., supra (2001) or in Ausubel et al., supra (1998). Additionally, relatively undamaged nucleic acids such as RNA can be obtained from a cell lysed by an enzyme that degrades the cell wall. Cells lacking a cell wall either naturally or due to enzymatic removal can also be lysed by exposure to osmotic stress. Other conditions that can be used to lyse a cell include exposure to detergents, mechanical disruption, sonication, heat, pressure differential such as in a French press device, or Dounce homogenization.

According to another aspect of the present invention, total RNA may be prepared using guanidine isothiocyanate, phenol:chloroform, and an inert carrier such as glycogen or linear polyacrylamide. For instance, about 20 ng of glycogen per 1 ml (reaction volume) may be added during alcohol precipitation to increase recovery of total RNA. Samples may then be prepared by commercially available column-based purification methods, such as the miRACLE miRNA Purification Kit from STRATAGENE (La Jolla, Calif.). Isolated RNA may be diluted in TE buffer or RNase-free water, for example, and stored appropriately.

Agents that stabilize nucleic acids can be included in a cell lysate or other biological isolate including, for example, nuclease inhibitors such as ribonuclease inhibitors or deoxyribonuclease inhibitors, chelating agents, salts buffers and the like. Methods for lysing a cell to obtain nucleic acids can be carried out under conditions known in the art as described, for example, in Sambrook et al., supra (2001) or in Ausubel et al., supra, (1998).

In another aspect of the present invention, a biological isolate can be a crude cell lysate obtained without further isolation of nucleic acids. Alternatively, a nucleic acid of interest can be further isolated from other cellular components according to the present invention. The method 10 of the present invention can be carried out on purified or partially purified RNA. RNA can be isolated using known separation methods including, for example, liquid phase extraction, precipitation or solid phase extraction. Such methods are described, for example, in Sambrook et al., supra, (2001) or in Ausubel et al., supra, (1998) or available from various commercial vendors including, for example, Qiagen (Valencia, Calif.) or Promega (Madison, Wis.).

If desired, nucleic acids can be separated based on properties such as mass, charge to mass, or the presence of a particular sequence. Methods for separating nucleic acids include, but are not limited to, electrophoresis using agarose or polyacrylamide gels, capillary electrophoresis, conventional chromatography methods such as size exclusion chromatography, reverse phase chromatography or ion exchange chromatography or affinity methods such as affinity chromatography or precipitation using solid-phase poly dT oligonucleotides. Those skilled in the art will know or be able to determine an appropriate separation method or combination of separation methods to obtain a biological isolate of a desired nucleic acid composition and purity. Proteins and large genomic DNA can be removed from RNA, for example, using precipitation and centrifugation methods that exploit the larger size of the genomic DNA and proteins. Messenger RNA can be removed from other RNA species, for example, using precipitation with poly dT oligonucleotide beads or size exclusion chromatography. Such methods can be used in combination with selective modification of the 5' phosphate of small oligonucleotides to distinguish small oligonucleotides from other cellular components.

At 30, the biological isolate is contacted with a labeled detection oligonucleotide and a bridge oligonucleotide to capture a small oligonucleotide from the biological isolate. By "capture" it is meant that a nucleic acid, such as a small oligonucleotide, hybridizes to a complementary nucleic acid, such as the bridge oligonucleotide.

The detection oligonucleotide may be prepared under conditions such that the 5' phosphate and/or the 3' hydroxyl of the detection oligonucleotide is/are preferentially modified to include a label moiety. Optionally or additionally, the label moiety may be internally incorporated into the detection oligonucleotide. According to another aspect of the present invention, a phosphate reactive reagent comprising a label moiety or label precursor moiety can be used so that 5' phosphate modification produces a detection oligonucleotide containing the label moiety. The detection oligonucleotide may also be prepared such that the 5' end or the 3' end includes a modification (e.g., inverted dTs) that prevents or reduces the formation of side ligation products.

By way of example, the detection oligonucleotide may be generated by 5' end-labeling a DNA oligonucleotide with [$\gamma$-$^{32}$P]-ATP, including an inverted dT at the 3' end, and then removing any unincorporated isotope. Briefly, reagents (i.e., the detection oligonucleotide, RNase-free water, 10× OPTIKINASE Reaction Buffer, [$\gamma$-$^{32}$P]-ATP, and OPTIKINASE) may be thawed on ice, mixed thoroughly, briefly spun, and then combined at room temperature. The mixture may then be incubated for about 30 to 60 minutes. After incubation, aliquots of the mixture may be treated to remove unincorporated [$\gamma$-$^{32}$P]-ATP. Thereafter, a population of labeled detection oligonucleotides may be generated and used as described below.

It should be understood that a variety of phosphate reactive reagents may be used with the present invention. Generally, the phosphate reactive reagent can preferentially add a moiety to a phosphate in a reaction mixture. For example, a phosphate reactive agent can be added to a population of detection oligonucleotides so that it preferentially reacts with the 5' phosphate of the detection oligonucleotide. Phosphate reactive reagents can include those that are unreactive to the 3' end of nucleic acids.

A phosphate reactive reagent can be a single molecule or a combination of molecules. For example, a single molecule can contain a reactive moiety linked to a label moiety such that reaction between the reactive moiety and the 5' phosphate of the detection oligonucleotide produces a detection oligonucleotide linked to the label moiety.

Alternatively, a combination of molecules can be used as a phosphate reactive reagent. For example, a first label molecule can be contacted with a detection oligonucleotide and a second molecule that activates the 5' phosphate or the first label molecule, thereby producing a detection oligonucleotide with an attached label. The phosphate reactive reagent can additionally or alternatively include a label moiety having a linked amino group and a second molecule being a carbodiimide molecule that activates the 5' phosphate to react with the amino group to produce a detection oligonucleotide having a phosphoramidite linkage to the label moiety. Other exemplary phosphate reactive reagents include, without limitation, $\epsilon$-(6-(biotinoyl)amino)hexanoyl-L-lysine, hydrazide; DSB-X biotin hydrazide; DSB-X desthiobiocytin (-desthiobiotinoyl-L-lysine); DSB-X biotin ethylenediamine (desthiobiotin-X ethylenediamine, hydrochloride); Biotin-X cadaverine; Alexa Fluor cadaverine; 5-(aminoacetamido) fluorescein(fluoresceinyl glycine amide); 4'-(aminomethyl) fluorescein, hydrochloride; 5-(((2-(carbohydrazino)methyl) thio)acetyl)aminofluorescein; fluorescein-5-thiosemicarbazide; N-methyl-4-hydrazino-7-nitrobenzofurazan; Oregon Green 488 cadaverine; 5-((5-aminopentyl)thioureidyl)eosin, hydrochloride; Texas Red cadaverine; Texas Red hydrazide; bimane amine; poly(ethylene glycol) methyl ether, amine-terminated; and Lissamine rhodamine B ethylenediamine. Those skilled in the art will recognize that any of a variety of label moieties can be replaced for those listed in these reagents. For example, fluorescein can be replaced with other fluorophores described herein.

The bridge oligonucleotide may be a DNA oligonucleotide complementary to both the detection oligonucleotide and a specific small oligonucleotide at the 5' and 3' ends of the bridge oligonucleotide, respectively. Alternatively, the bridge oligonucleotide can be complementary to both the detection oligonucleotide and a small oligonucleotide at the 3' and 5' ends, respectively. It should be that where, for example, the label moiety is attached to the phosphate group at the 5' end of the detection oligonucleotide, and the bridge oligonucleotide is designed to join the detection oligonucleotide to the 3' hydroxyl group of the small oligonucleotide, that the phosphate-labeled moiety should not have properties that prevent a ligation reaction.

By way of example, a small oligonucleotide can be captured by combining a biological isolate with a labeled detection oligonucleotide and a bridge oligonucleotide. A positive control containing a small oligonucleotide of interest and negative control (i.e., not containing RNA) may also be prepared. The reaction mixture may then be mixed, briefly spun, and incubated for a desired period of time at an appropriate temperature. A small oligonucleotide may be captured by the bridge oligonucleotide by hybridizing to the 3' end of the bridge oligonucleotide. The labeled detection oligonucleotide may also hybridize to the 5' end of the bridge oligonucleotide either before, simultaneous with, or after the small oligonucleotide has been captured. Alternatively, a small oligonucleotide may be captured by the bridge oligonucleotide by hybridizing to the 5' end of the bridge oligonucleotide. In this case, the labeled detection oligonucleotide may hybridize to the 3' end of the bridge oligonucleotide either before, simultaneous with, or after the small oligonucleotide has been captured.

After incubating the reaction mixture, at least one ligating reagent may be added to the reaction mixture at 40. A "ligating reagent" as used herein refers to a molecule, typically an enzyme, capable of facilitating phosphodiester bond formation between two nucleotides. Examples of ligating reagents include DNA ligases, such as T4 DNA ligase, which may form covalent phosphodiester bonds between the 3' hydroxyl end of one nucleotide and the 5' phosphate end of another nucleotide. Other examples of ligating reagents include RNA ligase, DNA ligases I-IV, as well as chemical cross-linking agents known in the art.

Following capture of the small oligonucleotide, at 40, the captured small oligonucleotide and the labeled detection oligonucleotide are ligated to form a labeled small oligonucleotide. The captured small oligonucleotide and the labeled detection oligonucleotide can be ligated by combining the captured small oligonucleotide and the labeled detection oligonucleotide with at least one ligating reagent. The at least ligating reagent can include, for example, a composition comprising T4 DNA ligase. The ligating reagent may be added to the reaction mixture, and the resultant reaction mixture briefly spun and incubated for a desired period of time at an appropriate temperature. By adding the ligating reagent to the reaction mixture, the 5' phosphate of the detection oligonucleotide and the 3' hydroxyl of the small oligonucleotide form a covalent phosphodiester bond so that the 5' and 3' ends of the detection oligonucleotide and the small oligonucleotide are respectively ligated. Alternatively, where the detection oligonucleotide and the small oligonucleotide are respectively hybridized to the 3' and 5' ends of the bridge oligonucleotide, the 3' hydroxyl of the detection oligonucleotide and the 5' phosphate of the small oligonucleotide may form a covalent phosphodiester bond so that the 3' and 5' ends of the detection oligonucleotide and the small oligonucleotide are respectively ligated.

In one example, the size of the ligated small oligonucleotide and detection oligonucleotide can be about 35 to about 39 nucleotides (e.g., about 21 to about 25 nucleotides of the small oligonucleotide plus about 14 nucleotides of the labeled detection oligonucleotide). It will be appreciated that the size of the ligated small oligonucleotide and the detection oligonucleotide can be smaller or larger depending on the size of the small oligonucleotide and the detection oligonucleotide.

Following ligation of the captured small oligonucleotide and the labeled detection oligonucleotide, excess detection oligonucleotides and/or labeled moieties from any unligated detection oligonucleotides of the reaction mixture can be removed. The excess labeled moieties can be removed using, for example, a clean-up reagent comprising a phosphatase. The phosphatase can remove phosphate groups from the 5' ends of small oligonucleotides containing phosphate-labeled moieties. Removal of labeled phosphate groups can prevent interference with small oligonucleotide detection and analysis. It should be appreciated that clean-up reagents may not be required depending upon the properties of the label moiety and/or where the label moiety is incorporated. Upon removing any unligated detection oligonucleotides from the reaction mixture, a plurality of labeled small oligonucleotides is generated that can be subsequently detected.

Following ligation, at 50, the labeled small oligonucleotides can be detected. The labeled small oligonucleotide can be detected and distinguished from other molecules that are devoid of a label using methods known in the art. Exemplary properties upon which detection can be based include, but are not limited to, mass, electrical conductivity or optical signals, such as a fluorescent signal, absorption signal, luminescent signal, chemiluminescent signal or the like. Detection can also be based on absence or reduced level of one or more signal, for example, due to the presence of a signal quenching moiety or degradation of a label moiety.

Various detection methods, such as solution phase and solid phase assays, may be used to detect labeled small oligonucleotides. Solution phase detection methods can be based on charge, mass, charge-to-mass ratio or other distinguishing properties. Such distinguishing properties can be detected, for example, in a chromatography system such as capillary electrophoresis, acrylamide gel, agarose gel, or the like, or in a spectroscopic system such as mass spectroscopy.

For example, detection of fluorescence can be carried out by irradiating a labeled small oligonucleotide with an excitatory wavelength of radiation and detecting radiation emitted from a fluorophore therein by methods known in the art and described in Lakowicz, Principles of Fluorescence Spectroscopy, 2nd Ed., Plenum Press New York (1999). A fluorophore can be detected based on any of a variety of fluorescence phenomena including, for example, emission wavelength, excitation wavelength, fluorescence resonance energy transfer (FRET) intensity, quenching, anisotropy or lifetime. FRET can be used to identify hybridization between a first oligonucleotide attached to a donor fluorophore and a second oligonucleotide attached to an acceptor fluorophore due to transfer of energy from the excited donor to the acceptor. Thus, hybridization can be detected as a shift in wavelength caused by reduction of donor emission and appearance of acceptor emission for the hybrid.

In another aspect of the present invention, the labeled small oligonucleotide can be detected using gel electrophoresis. Briefly, a UREA-polyacrylamide gel of about 12% to 15% may be prepared and then loaded with samples of a reaction mixture containing labeled small oligonucleotides. The gel may be run using appropriate amperage until each sample has reached an appropriate end-point on the gel. The resultant gel may be transferred onto a sheet of non-diffusible support material, such as processed film, and then developed by exposure to X-ray or a phosphorimager screen for an appropriate amount of time. After developing the gel, the presence of darkened bands at known positions on the gel may indicate the presence of small oligonucleotides in the biological isolate.

Figure 2A:
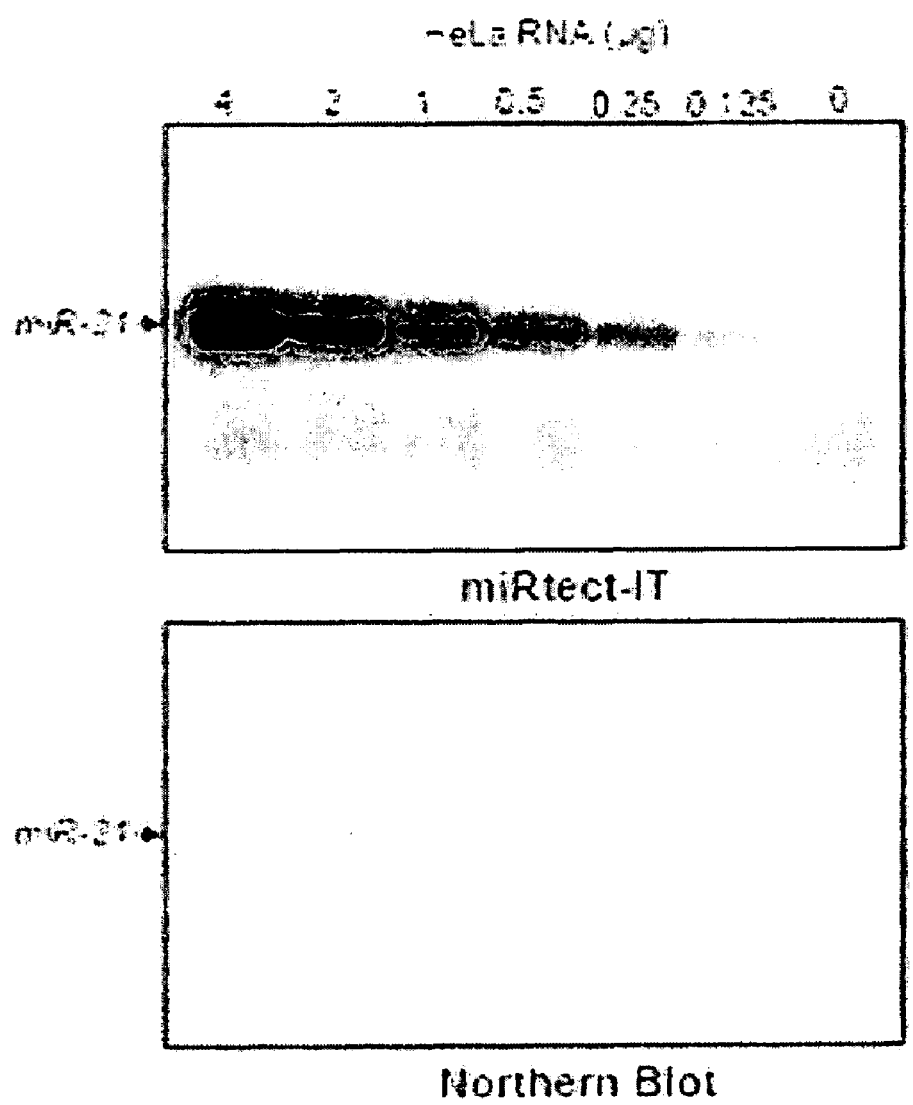
Figure 3:
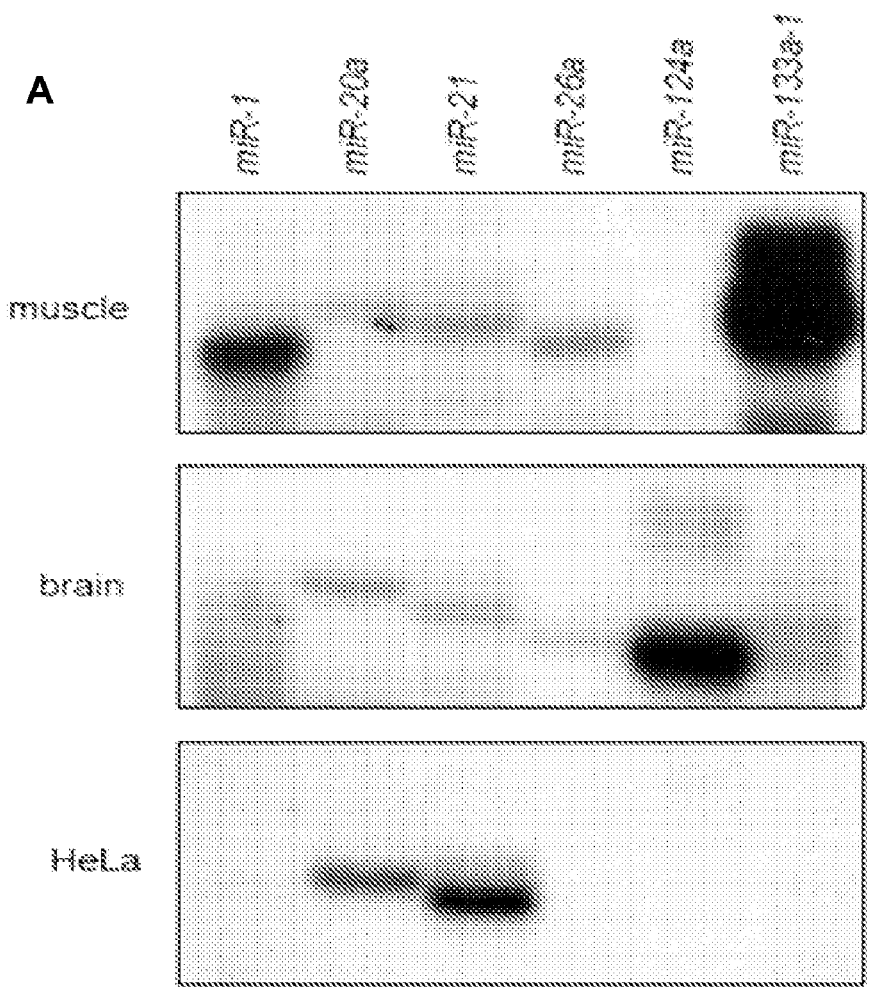
FIGS. 3A-B show miRNA expression profiles in muscle tissue (FIG. 3A, upper), brain tissue (FIG. 3A, middle), and HeLa cells (FIG. 3A, lower) using the present invention.

The present invention provides a fast and efficient method for detecting small oligonucleotides over the standard technique for small oligonucleotide expression analysis, i.e., Northern blotting. Northern blotting exhibits poor sensitivity, requires large amounts of total RNA, and is both labor intensive and time-consuming. As illustrated in FIGS. 2A-C, the present invention provides a 50-fold better detection sensitivity than Northern blotting. Additionally, the present invention significantly reduces both the total reaction time and the amount of total RNA needed to perform the assay. Referring to FIGS. 3A-B, for example, the amount of total RNA needed with the present invention is only 18 µg, whereas 180 µg of total RNA is needed for Northern blotting. Similarly, the reaction time needed with the present invention is only 2-4 hours, whereas the reaction time needed for Northern blotting is 2-3 days.

As noted, other detection methods, such as solid phase assays, may be used to detect small oligonucleotides. For example, different types of arrays may be used. An "array" refers to a population of different probe molecules that are attached to one or more substrates such that the different probe molecules can be differentiated from each other according to relative location. An array can include different probe molecules that are each located at a different addressable location on a substrate. Alternatively, an array can include separate substrates each bearing a different probe molecule. Probes attached to separate substrates can be identified according to the locations of the substrates on a surface to which the substrates are associated or according to the locations of the substrates in a liquid. Exemplary arrays in which separate substrates are located on a surface include, without limitation, those including beads in wells.

Another aspect of the present invention may include a kit for detecting a plurality of different small oligonucleotides. The kit may include a detection oligonucleotide, a label moiety for preferentially labeling the detection oligonucleotide, and reagents for ligating the 3' end of the small oligonucleotide to the 5' end of the detection oligonucleotide.

In another aspect of the present invention, the kit may include additional components, including, for example, reagents for removing unbound label moieties, reagents for removing non-ligated detection oligonucleotides, reagents for detecting labeled small oligonucleotides, a positive control, and a negative control. The positive control may be used to assess kit components and procedure, while the negative control may be used to assess background signal(s) in tested samples.

Figure 4:
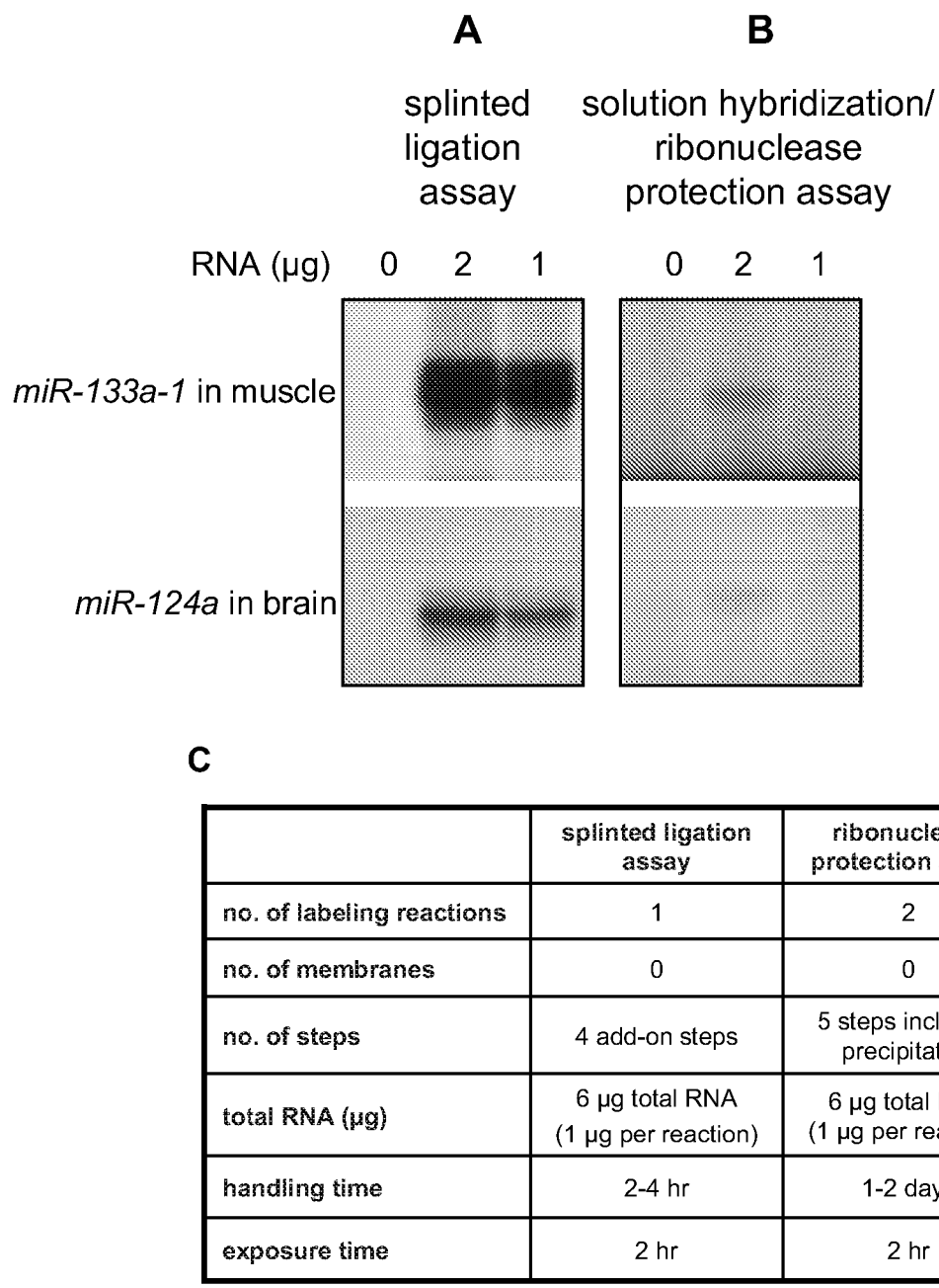
FIGS. 4A-C illustrate a comparative example of the present invention and a solution hybridization/ribonuclease protection assay.

Commercially available kits for detecting small oligonucleotides include solution hybridization/ribonuclease protection assays such as the mirVana miRNA Isolation Kit available from Ambion (Austin, Tex.). The present invention provides several advantages over such commercial assays. When compared to the mirVana miRNA Isolation Kit, for example, the present invention provides greater miRNA detection sensitivity in a shorter reaction period. As shown in FIGS. 4A-C, the mirVana miRNA Isolation Kit not only exhibits poorer sensitivity in a longer reaction period, but also requires the separate purchase of a labeling kit and optimization of the amount of labeled probe, hybridization conditions, and the amount of ribonuclease.

Throughout this application various publications, patents and patent applications have been referenced. The disclosures of these publications in their entireties are hereby incorporated by reference in this application in order to more fully describe the state of the art to which this invention pertains.

The following examples are for the purpose of illustration only and are not intended to limit the scope of the claims, which are appended hereto.

EXAMPLE 1

Detection Oligo Preparation and Clean-Up

The first step is to 5' end-label the Detection Oligo with [$\gamma$-$^{32}$P]-ATP and remove unincorporated isotope.

1. Thaw frozen reagents on ice, mix thoroughly followed by a brief spin, and then place on ice.
2. Prepare [$^{32}$P]-labeled Detection Oligo by combining the following components at room temperature:

| Components | Detection Oligo | Component Cap Color |
|---|---|---|
| Detection Oligo | 2 µl | Blue |
| RNase Free Water | 12 µl | White |
| 10X OPTIKINASE Reaction Buffer | 2 µl | Blue |
| [$\gamma$-$^{32}$P]-ATP (6000 Ci/mMol, 150 mCi/ml) | 2 µl | Not Supplied |
| OPTIKINASE | 2 µl | Blue |
| Total volume | 20 µl | |

3. Mix thoroughly followed by a brief spin in a microcentrifuge. Incubate for 30-60 mm at 37° C.
4. While the reactions are incubating, prepare the Clean-Up Column as follows:
   a. Centrifuge the Clean-Up Column for 30 sec at 750×g to collect the dry resin at the bottom of the column.
   b. Hydrate the resin by adding 600 µl RNase-Free Water and vortex. Remove air bubbles by vortexing or tapping the column. Incubate at least 30 mm at room temperature.
   c. Re-suspend the settled resin by inverting the column several times. Ensure that no air bubbles are visible. Remove the bottom plug and place in a 2.0 ml collection tube.
   d. Centrifuge for 2 mm at 750×g to remove the remaining water. Discard the flow-through.
5. After 30 mm incubation, dilute the labeling reactions to 100 µl by adding 80 µl of RNase-Free Water.
6. Place the column from Step 4d in a clean 1.5 ml microcentrifuge tube. Without disturbing the gel bed, carefully apply the diluted sample directly onto the top of the gel bed.
7. After loading the sample, centrifuge the column for 4-6 mm at 750×g. Discard the used column in a radioactive waste container.
8. The radiolabeled Detection Oligo and Marker are now ready to use.

EXAMPLE 2 miRNA Capture, Ligation and Clean-Up

Once the Detection Oligo is radiolabeled, proceed to the miRNA detection assay.

Design and Preparation on page 12. The Bridge Oligonucleotide should be diluted to 0.1 pmol/µl with the provided 10× Capture Buffer.

1. Thaw frozen reagents on ice, mix thoroughly followed by a brief spin, and then place on ice.
2. Assemble the capture reaction on ice according to the table below:

| Components | Positive Control | No RNA Control | Sample | Component Cap Color |
|---|---|---|---|---|
| Total RNA Sample | 0 µl | 0 µl | up to 8 µl | Not Supplied |
| Positive Control Adjust to 8 µl with RNASE-Free Water | 1 µl | 0 µl | 0 µl | Red White |
| 0.1 pmol/µl Bridge Oligo in 10X Capture Butter | 1 µl | 1 µl | 1 µl | Not Supplied |
| Radio-labeled Detection Oligo | 1 µl | 1 µl | 1 µl | N/A |
| Total Volume | 10 µl | 10 µl | 10 µl | |

Make a Bridge Oligonucleotide-Detection Oligo Master Mix for assay setup. Per sample combine: 1 µl Bridge Oligonucleotide in 10X Capture Buffer + 1 µl radiolabeled Detection Oligo.
Dilute all test samples to 8 µl with RNase-Free Water then add 2 µl of the Bridge Oligonucleotide-Detection Oligo Master Mix.

3. Mix thoroughly followed by a brief spin in a microcentrifuge. Incubate the mixture at 94° C. for 1 min, 65° C. for 2 min and 37° C. for 10 min. For convenience, a thermalcycler may be used.
4. Add 5 µl of 3× Ligate-IT™ Premix (red cap) to each reaction.
5. Mix thoroughly followed by a brief spin. Incubate for 1 hr at 30° C. Optional: If not proceeding to the next step immediately, inactivate the reaction by incubation for 10 min at 75° C. and store at −20° C. for later use.
6. Add 1 µl of Clean-Up Mix (red cap) to each reaction.
7. Mix thoroughly followed by a brief spin. Incubate for 15 mm at 37° C. Optional: If not proceeding to the next step immediately, inactivate the reaction by incubation for 10 min at 75° C. and store at −20° C. for later use.
8. The ligated miRNA is now ready for gel electrophoresis.

EXAMPLE 3

Electrophoretic Analysis

1. Prepare a 12% or 15% UREA-polyacrylamide gel with 1× running buffer. (See Supplementary Information on Preparation of UREA-polyacrylamide gel) Optional: Pre-run and warm the gel for 30 minutes.
2. Transfer a 3-15 pl aliquot of the reaction to a new tube. Add an equal volume of Gel Loading Dye.
3. Transfer an aliquot of the [$^{32}$P]-labeled Low Molecular Weight Marker to a new tube. Add an equal volume of Gel Loading Dye.
4. Mix thoroughly followed by a brief spin in a microcentrifuge. Incubate for 3 min at 95° C. Immediately cool on ice.
5. Flush wells of the gel to remove acrylamide debris, urea and air bubbles.
6. Load and separate the denatured reactions. Include the [$^{32}$P]-labeled Low Molecular Weight Marker on each gel. The expected size of ligated miRNA is 35-39 nucleotides (21-25 nucleotides of mature miRNA sequence plus 14 nucleotides of the labeled Detection Oligo).

In 12% and 15% gels, the approximate band positions of bromophenol blue and xylene cyanol (loading dyes) are 10 and 30 nucleotides, respectively.

For 13 cm×15 cm gel, run at 20-30 mA and stop when the bromophenol blue dye front has migrated to the bottom of the gel. For 36 cm×43 cm gel, run at 60 mA and stop when the bromophenol blue dye front has migrated to the middle of the gel.

7. At the end of the separation, transfer the gel onto a sheet of non-diffusible support material such as processed film. Wrap with saran wrap and expose to X-ray film or a phosphorimager screen.

It is unnecessary to dry the gel if using [$^{32}$P]-isotope. Expose the gel to X-ray film with an intensifying screen. Store for 2 hr to overnight at −80° C. The gel can be re-exposed several times if required.

It is recommended to dry the gel if using a phosphorimager screen to prevent screen damage. Process the phosphorimager screen according to the manufacturer's instructions.

From the above description of the invention, those skilled in the art will perceive improvements, changes and modifications. Such improvements, changes and modifications within the skill of the art are intended to be covered by the appended claims. All references, patents, and publications cited herein are incorporated by reference in their entirety.

Having described the invention, the following is claimed:

1. A method for detecting at least one small oligonucleotide in a biological isolate, comprising:

providing a biological isolate that includes at least one small oligonucleotide;

adding at least one detection oligonucleotide having a label moiety and at least one bridge oligonucleotide, the bridge oligonucleotide complementary to the detection oligonucleotide and the at least one small oligonucleotide, to the biological isolate under conditions such that the at least one small oligonucleotide and the at least one detection oligonucleotide are preferentially captured by the bridge oligonucleotide to produce at least one labeled small oligonucleotide;

adding at least one ligating reagent to preferentially join the at least one captured small oligonucleotide and the at least one captured detection oligonucleotide bound to the bridge oligonucleotide;

adding at least one clean-up reagent, the at least one clean-up reagent removing the label moiety from at least one detection oligonucleotide that is not ligated to at least one small oligonucleotide;

detecting the at least one labeled small oligonucleotide; and determining the amount of small oligonucleotide in the biological isolate.

2. The method of claim 1, the at least one small oligonucleotide comprising DNA, small regulatory RNA, non-coding RNA, microRNA or small interfering RNA.

3. The method of claim 1, the at least one detection oligonucleotide and/or the at least one bridge oligonucleotide comprising DNA, RNA, modified nucleotides, or a combination of DNA, RNA, and modified nucleotides.

4. The method of claim 1, the at least one detection oligonucleotide comprising about 5 to about 500 nucleotides.

5. The method of claim 4, the at least one detection oligonucleotide having a 5' end, a 3' end, and a label moiety, label moiety being linked to the 5' end.

6. The method of claim 5, the 5' end of the detection oligonucleotide being linked to the label moiety via a phosphoramide linkage.

7. The method of claim 1, the at least one detection oligonucleotide further including at least one of a C-3 spacer, an amino modifier, an inverted dT, a dideoxy-C, or an agent that prevents a side ligation reaction.

8. The method of claim 5, the 5' end of the detection oligonucleotide being linked to a 3' end of the at least one small oligonucleotide by the at least one ligating reagent.

9. The method of claim 5, the label moiety comprising an optically detectable moiety selected from the group consisting of a chromophore, a luminophore, a fluorophore, a quantum dot or nanoparticle light scattering label, an electromagnetic spin label, a calorimetric agent, a magnetic substance, an electron-rich material, an electrochemiluminescent label, a label that can be detected based on nuclear magnetic, paramagnetic, electrical, charge to mass, or thermal characteristics, and light scattering or plasmon resonant materials.

10. The method of claim 9, the label moiety comprising an isotopic label selected from the group consisting of $^{14}$C, $^{123}$I, $^{124}$I, $^{125}$I, $^{131}$I, $^{32}$P, $^{33}$P, $^{35}$S, and $^{3}$H.

11. A method for detecting at least one small oligonucleotide in a biological isolate, comprising:

providing a biological isolate that includes at least one small oligonucleotide;

adding at least one detection oligonucleotide and at least one bridge oligonucleotide, the bridge oligonucleotide complementary to the detection oligonucleotide and the at least one small oligonucleotide, to the biological isolate under conditions such that the at least one small oligonucleotide and the at least one detection oligonucleotide are preferentially captured by the bridge oligonucleotide to produce at least one labeled small oligonucleotide, the at least one detection oligonucleotide having a 5' end, the 5' end including a phosphate group, a 3' end, and a label moiety, label moiety being linked to the 5' end of the detection oligonucleotide;

adding at least one ligating reagent to preferentially join the at least one captured small oligonucleotide and the at least one captured detection oligonucleotide bound to the bridge oligonucleotide;

adding at least one clean-up reagent comprising a phosphatase to remove the phosphate group from the 5' end of at least one detection oligonucleotide that is not ligated to at least one small oligonucleotide;

detecting the at least one labeled small oligonucleotide; and determining the amount of small oligonucleotide in the biological isolate.

12. The method of claim 11, the at least one small oligonucleotide comprising DNA, small regulatory RNA, non-coding RNA, microRNA or small interfering RNA.

13. The method of claim 11, the at least one detection oligonucleotide comprising about 5 to about 500 nucleotides.

14. The method of claim 11, the 5' end of the detection oligonucleotide being linked to the label moiety via a phosphoramide linkage.

15. The method of claim 11, the at least one detection oligonucleotide further including at least one of a C-3 spacer, an amino modifier, an inverted dT, a dideoxy-C, or an agent that prevents a side ligation reaction.

16. The method of claim 11, the 5' end of the detection oligonucleotide being linked to a 3' end of the at least one small oligonucleotide by the at least one ligating reagent.

17. The method of claim 11, the label moiety comprising an optically detectable moiety selected from the group consisting of a chromophore, a luminophore, a fluorophore, a quantum dot or nanoparticle light scattering label, an electromagnetic spin label, a calorimetric agent, a magnetic substance, an electron-rich material, an electrochemiluminescent label, a label that can be detected based on nuclear magnetic, paramagnetic, electrical, charge to mass, or thermal characteristics, and light scattering or plasmon resonant materials.

18. The method of claim 11, the label moiety comprising an isotopic label selected from the group consisting of $^{14}C$, $^{123}I$, $^{124}I$, $^{125}I$, $^{131}I$, $^{32}P$, $^{33}P$, $^{35}S$, and $^3H$.

* * * * *